US00PP28619P3

(12) United States Plant Patent
Dobres et al.

(10) Patent No.: US PP28,619 P3
(45) Date of Patent: Nov. 7, 2017

(54) ***SALVIA* PLANT NAMED 'NOVASALFUC'**

(50) Latin Name: *Salvia hybrida*
Varietal Denomination: Novasalfuc

(71) Applicant: CP DELAWARE, INC., Wilmington, DE (US)

(72) Inventors: Michael S. Dobres, San Javier (ES); Jessica D. Janes, Elkton, MD (US)

( * ) Notice: Subject to any disclaimer, the term of this patent is extended or adjusted under 35 U.S.C. 154(b) by 15 days.

(21) Appl. No.: 14/757,359

(22) Filed: Dec. 22, 2015

(65) Prior Publication Data

US 2017/0181355 P1 Jun. 22, 2017

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Buchanan Ingersoll & Rooney PC

(57) ABSTRACT

A new and distinct *Salvia* plant was formed by controlled breeding followed by selection. Over a long blooming season attractive fuchsia colored blossoms with dark calyxes are formed. The growth habit is well-branched compact and bushy. The blossoms are borne on sturdy stems. Attractive green foliage is formed. The plant can be readily asexually reproduced by the rooting of cuttings. Hardiness to at least U.S.D.A. Hardiness Zone No. 7 is displayed. The plant is well suited for providing attractive ornamentation in parks, gardens, public areas, and residential landscapes.

2 Drawing Sheets

Botanical/commercial classification: *Salvia hybrida/Salvia* Plant.

Varietal denomination: cv. Novasalfuc.

SUMMARY OF THE INVENTION

The new cultivar of *Salvia hybrida* was created by artificial pollination carried out at West Grove, Pa., U.S.A., during October 2010 wherein two parents were crossed which previously had been studied in the hope that they would contribute desired characteristics. The female parent (i.e., seed parent) was the *Salvia greggii* 'Furman's Red' cultivar (non-patented). The male parent (i.e., pollen parent) was the 'Golden Girl' cultivar (U.S. Plant Pat. No. 23,997, granted Oct. 15, 2013).

The parentage of the new cultivar can be summarized as follows:

'Furman's Red'×'Golden Girl'.

The seeds resulting from the pollination were collected during November 2010, were grown in tissue culture, and small plants were obtained which were acclimated to greenhouse conditions in November 2010 and were physically and biologically different from each other. Selective study resulted in the identification of a single plant of the new cultivar. A plant of the present invention was selected during July 2011 primarily in view of its abundance of attractive hot pink flowers, long blooming period, and well branched and sturdy stems. Had this new plant not been selected and preserved, it would have been lost to mankind.

The plant is a perennial that can be grown to advantage without protection to U.S.D.A. Hardiness Zone No. 7. Established plants appear to exhibit adaptability to U.S.D.A. Hardiness Zone No. 6 during observations to date.

It was found that the new *Salvia* cultivar possesses the following combination of characteristics:

(a) displays a well-branched compact and bushy growth habit with sturdy stems,
(b) forms in abundance attractive fuchsia colored blossoms with dark calyxes over an extended blooming season,
(c) displays hardiness to at least U.S.D.A. Hardiness Zone No. 7,
(d) forms attractive green foliage, and
(e) is well suited for providing attractive ornamentation.

The new cultivar of the present invention can be readily distinguished from other *Salvia* cultivars, such as the 'Furman's Red' cultivar and the 'Golden Girl' cultivar. More specifically, the 'Furman's Red' cultivar displays blossoms with more red rather than fuchsia, and the 'Golden Girl' cultivar displays dissimilar yellow blossoms. Additionally, while the new variety displays fuchsia colored blossoms, the 'Bright Eyes' variety of U.S. Plant Pat. No. 22,491 displays red blossoms with white eyes; the 'Orchid Glow' variety of U.S. Plant Pat. No. 22,520 displays purple blossoms; and the 'Lemon Light' variety of U.S. Plant Pat. No. 24,105 displays bright yellow blossoms.

The new cultivar well meets the needs of the horticultural industry and can be grown to advantage as attractive colorful ornamentation in parks, gardens, public areas, and residential landscapes.

The new cultivar has been asexually reproduced by the rooting of cuttings for several generations. Such asexual reproduction as performed at West Grove, Pa., U.S.A., has demonstrated that the characteristics of the new cultivar are firmly fixed and stable and are strictly transmissible from one generation to another. Accordingly, the new cultivar asexually reproduces in a true-to-type manner from one generation to another.

The new cultivar has been named 'Novasalfuc', and will be marketed under the FUSHSIA ARCTIC Trademark.

BRIEF DESCRIPTION OF THE PHOTOGRAPHS

The accompanying photographs show the new cultivar as nearly true as it is reasonably possible to make the same in color illustrations of this character. The plants were growing outdoors on their own roots at West Grove, Pa., U.S.A.

DETAILED BOTANICAL DESCRIPTION

Figure 1:
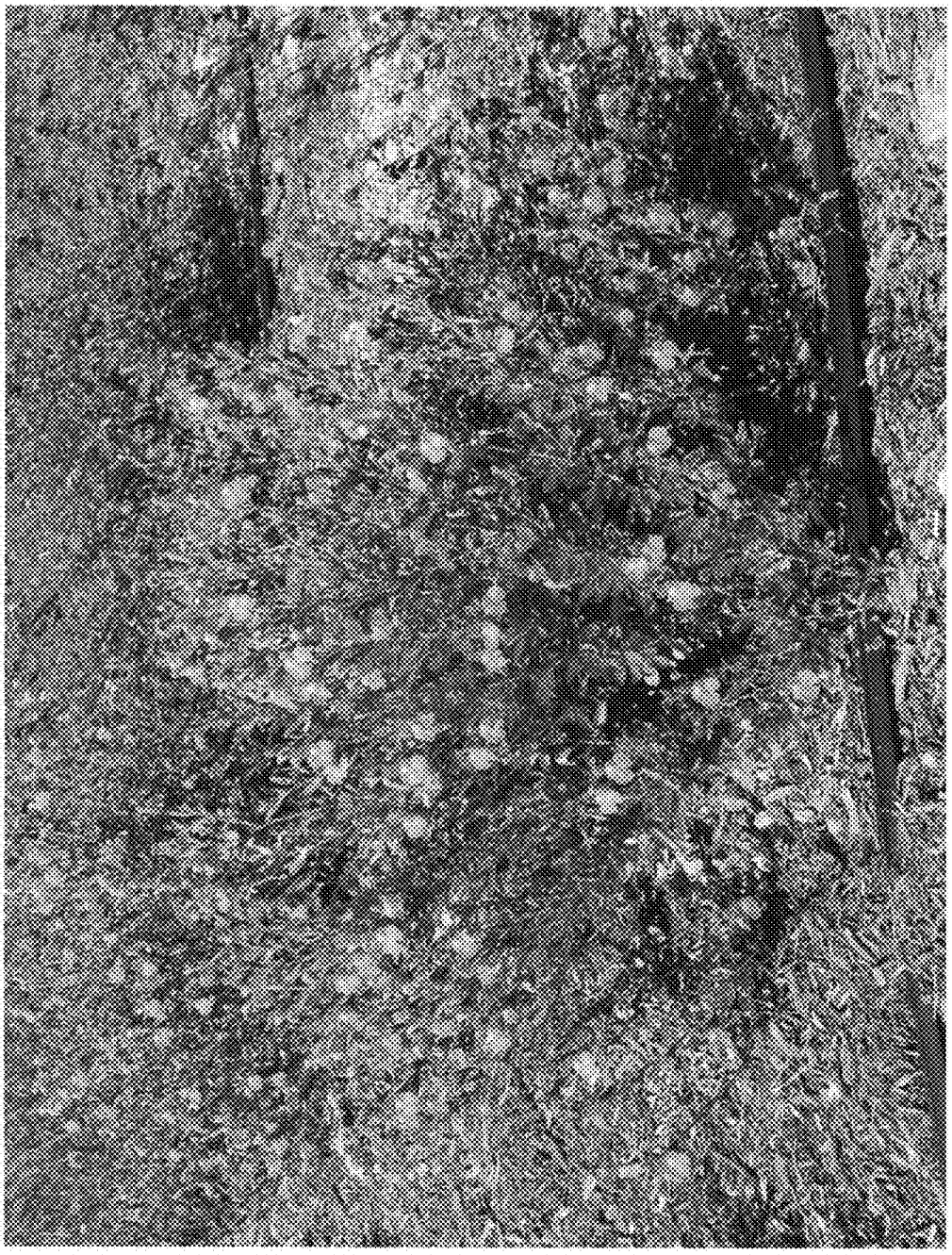
FIG. 1 illustrates the overall compact and bushy growth habit of a flowering plant of the new cultivar during October 2014 while growing in the ground.
Figure 2:
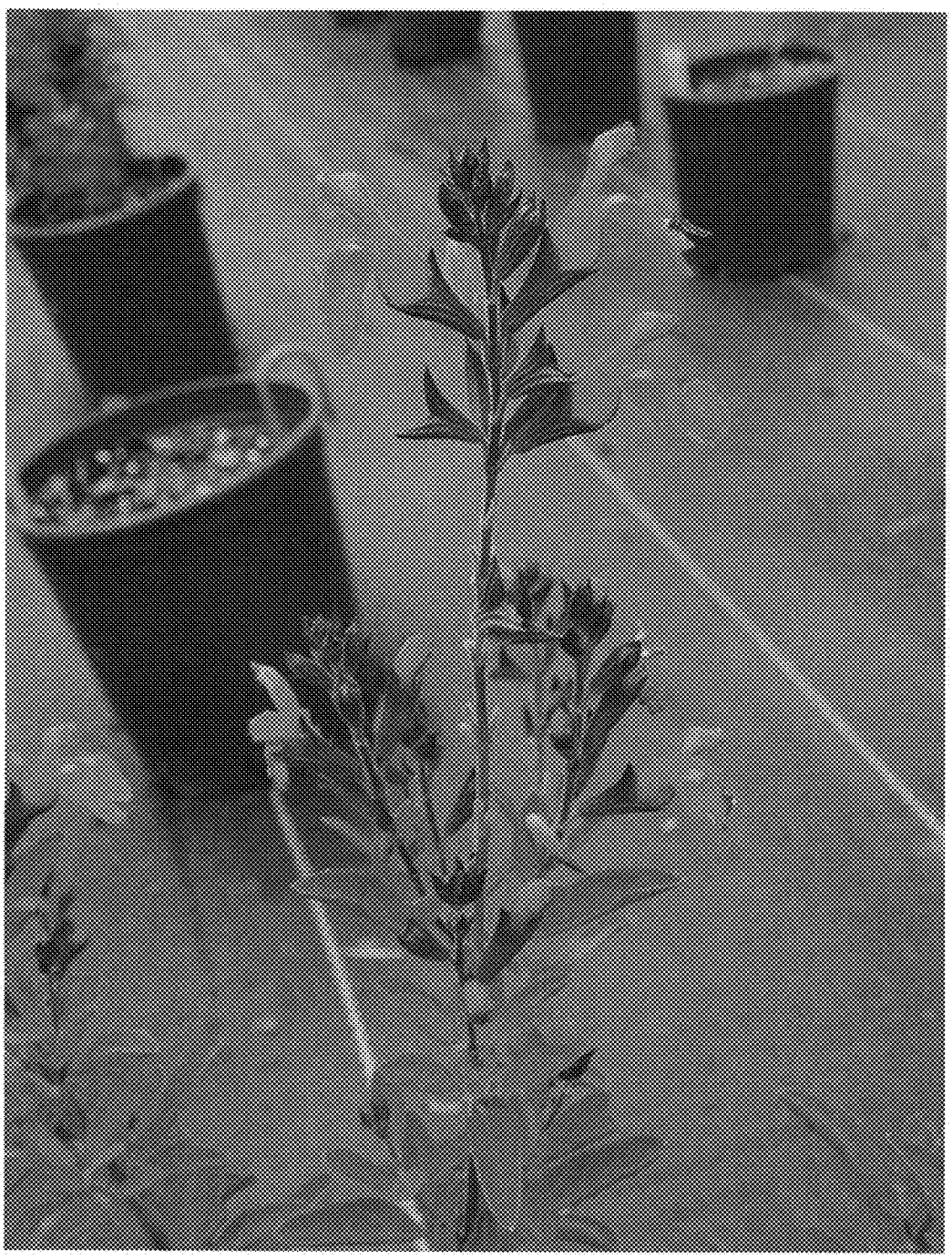
FIG. 2 illustrates a closer view of the attractive fuchsia blossoms with darker calyxes in various stages of development and foliage of the new cultivar during June 2015 while growing in a container.

The chart used in the identification of colors is that of The Royal Horticultural Society (R.H.S. Colour Chart) of London, England (1995). The description is based on the observation of typical specimens of the new cultivar at an age of approximately one year during August 2015 while growing outdoors in containers at West Grove, Pa., U.S.A.

Plant:

*Form*.—Compact and bushy.

*Height*.—Commonly approximately 40 cm on average.

*Width*.—Commonly approximately 45 cm on average.

*Growth habit*.—Perennial in U.S.D.A. Hardiness Zone Nos. 7 to 11 with established plants exhibiting adaptability in U.S.D.A. Hardiness Zone No. 6.

*Lateral branch number*.—23 on average per two-year-old in ground plant.

*Lateral branch color*.—Commonly near Brown Group N200B.

*Lateral branch texture*.—Commonly scabrous with older wood being more rugulose.

*Lateral branch length*.—Approximately 50 cm on average.

*Lateral branch diameter*.—Approximately 0.6 cm on average.

*Lateral branch internode length*.—Approximately 1.75-2.0 cm on average.

*Leaf arrangement*.—Opposite.

*Leaf configuration*.—Elliptic to oblong.

*Leaf length*.—Commonly approximately 4.2 cm on average.

*Leaf width*.—Commonly approximately 1 cm on average.

*Leaf margin*.—Entire.

*Leaf venation*.—Pinnipalmate pattern, and color is commonly near Yellow-Green Group 144A.

*Leaf texture*.—Commonly slightly fleshy.

*Leaf blade color*.—Near Green Group 137B on the upper surface, and near Green Group 138A on the under surface.

*Leaf blade apex*.—Acute to obtusely rounded.

*Leaf blade base*.—Mainly obtuse.

*Scent*.—Leaves commonly display a tangy fruity scent when crushed.

*Petiole shape*.—Somewhat flattened.

*Petiole length*.—Commonly approximately 1.3 cm on average.

*Petiole width*.—Commonly approximately 1 mm.

*Petiole color*.—Near Green Group 143C.

Inflorescence:

*Type*.—Terminal raceme.

*Diameter*.—Commonly approximately 5 cm on average.

*Length*.—Commonly approximately 27 cm on average.

*Number*.—Commonly up to approximately 100 flowers per plant on average are in bloom at a given time.

*Configuration*.—Tubular, and two-lipped.

*Flower bud shape*.—Typically teardrop.

*Flower bud color*.—Commonly near Red-Purple Group N66A.

*Flower bud length*.—Approximately 1.5 cm on average.

*Flower bud diameter*.—Approximately 0.5 cm on average on widest part.

*Pedicel length*.—Commonly approximately 4 mm on average.

*Pedicel width*.—Commonly approximately 0.5 mm on average.

*Pedicel color*.—Near Greyed-Orange Group 176B.

*Pedicel pubescence*.—Present, with pedicel being puberulent.

*Calyx shape*.—Broadly campanulate and flared towards the apex.

*Calyx rib number*.—Commonly 12 on average and longitudinally disposed.

*Calyx length*.—Commonly approximately 1.4 cm on average.

*Calyx width*.—Commonly approximately 8 mm on average.

*Calyx texture*.—Glandular and puberulent.

*Calyx color*.—On the upper lobe near Yellow-Green Group 146C blended with Greyed-Orange Group 176B, and on the lower lobes near Yellow-Green Group 146D blended with Greyed-Orange Group 176B.

*Calyx lobe number*.—3.

*Calyx upper lobe number*.—1.

*Calyx upper lobe shape*.—Acute.

*Calyx upper lobe length*.—Commonly approximately 14 mm on average.

*Calyx upper lobe width*.—Commonly approximately 6 mm on average.

*Calyx lower lobe number*.—2.

*Calyx lower lobe shape*.—Acute.

*Calyx lower lobe length*.—Commonly approximately 13 cm on average.

*Calyx lower lobe width*.—Commonly approximately 8 mm on average.

*Corolla shape*.—Tubular proximally to two-lipped distally.

*Corolla length*.—Commonly approximately 2.6 cm on average.

*Corolla color*.—The base commonly is near White Group 155C, the tube is near Red Group 54A, and the lower lip is near Red Group 54A.

*Corolla tube length*.—Approximately 1.2 cm on average.

*Corolla tube depth*.—Approximately 6 mm on average.

*Corolla tube lip number*.—3.

*Corolla upper lip number*.—1.

*Corolla upper lip shape*.—Hood-like.

*Corolla upper lip length*.—Commonly approximately 8 mm average.

*Corolla lower lip length*.—2, suborbicular.

*Corolla lower lip shape*.—Banner-like, and extended downward.

*Corolla lower lip outline*.—Obovate.

*Corolla lower lip length*.—Commonly approximately 1.4 cm on average.

*Corolla lower lip diameter at tip*.—Approximately 1.4 cm on average.

*Style length*.—Approximately 2.3 cm on average.

*Style width*.—Commonly less than 1 mm.

*Style color*.—Near White Group 155C blending into near Red Group 54A towards the stigma.

*Style attachment site*.—At four-lobed ovary between lobes.

*Ovary*.—Approximately 2 mm in length, approximately 1 mm in diameter, and near Yellow-Green Group 145A in coloration.

*Stamen number*.—1.

*Stamen shape*.—Seesaw-like.

*Filament length*.—Approximately 6 mm on average.

*Connective length*.—Approximately 8 mm on average.

*Anther length*.—Approximately 2 mm on average.

*Anther diameter*.—Approximately 1 mm on average.

*Anther color*.—Near Yellow-Orange Group 177A.

*Anther attachment site*.—At outer end of the connective.

*Pollen*.—Abundant.

*Fertility*.—Good, commonly with one or two seeds formed per calyx.

*Seed*.—Commonly oval in shape, and commonly 1-4 seeds per pod on average.

Development:

*Vegetation*.—Well-branched compact and bushy with sturdy stems.

*Blooming*.—Displays a strong propensity to reblossom from spring through fall.

*Number of days to initiate roots*.—Approximately 10-14 days on average.

*Number of days to produce a rooted cutting*.—Approximately 28-35 days on average.

*Winter hardiness*.—The plant is a perennial that can be grown in U.S.D.A. Hardiness Zone Nos. 7 to 11, and when plants are well adapted possibly in U.S.D.A. Hardiness Zone No. 6.

*Disease resistance*.—Typical for *Salvia* with no particular sensitivity to disease having been encountered during observations to date. The new 'Novasalfuc' cultivar has not been observed under all possible environmental conditions. Accordingly, it is possible that the phenotypic expression may vary somewhat with changes in light intensity and duration, cultural practices, and other environmental conditions.

We claim:

1. A new and distinct *Salvia* plant characterized by the following combination of characteristics:

(a) displays a well-branched compact and bushy growth habit with sturdy stems, (b) forms in abundance attractive fuchsia colored blossoms with dark calyxes over an extended blooming season, (c) displays hardiness to at least U.S.D.A. Hardiness Zone No. 7, (d) forms attractive green foliage, and (e) is well suited for providing attractive ornamentation; substantially as illustrated and described.

* * * * *